US008330120B2

(12) United States Patent
Nishino et al.

(10) Patent No.: US 8,330,120 B2

(45) Date of Patent: Dec. 11, 2012

(54) ELECTRON BEAM STERILIZER

(75) Inventors: Yukinobu Nishino, Kanazawa (JP); Tokuo Nishi, Kanazawa (JP); Yukihiro Yamamoto, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 440 days.

(21) Appl. No.: 12/450,338

(22) PCT Filed: Mar. 5, 2008

(86) PCT No.: PCT/JP2008/053973

§ 371 (c)(1),
(2), (4) Date: Jan. 27, 2010

(87) PCT Pub. No.: WO2008/117641

PCT Pub. Date: Oct. 2, 2008

(65) Prior Publication Data

US 2010/0140507 A1 Jun. 10, 2010

(30) Foreign Application Priority Data

Mar. 26, 2007 (JP) ................................ 2007-079888

(51) Int. Cl.
*G21K 5/04* (2006.01)
*A61L 2/08* (2006.01)

(52) U.S. Cl. ........... 250/455.11; 250/453.11; 250/492.3; 422/22; 422/23

(58) Field of Classification Search ............. 250/453.11, 250/454.11, 455.11, 492.1, 492.3, 493.1; 422/22, 23
See application file for complete search history.

(56) References Cited

U.S. PATENT DOCUMENTS

| | | | | |
|---|---|---|---|---|
| 4,439,686 | A * | 3/1984 | Cheever | 250/492.3 |
| 2007/0018115 | A1* | 1/2007 | Naka et al. | 250/454.11 |

FOREIGN PATENT DOCUMENTS

| | | |
|---|---|---|
| JP | 2006-199377 | 8/2006 |
| JP | 2007-029709 | 2/2007 |
| WO | 2005/086201 A1 | 9/2005 |

OTHER PUBLICATIONS

International Search Report dated Apr. 22, 2008 (3 pages).
Form PCT/ISA/220 (4 pages), Apr. 22, 2008.
Form PCT/ISA/237 (3 pages), Apr. 22, 2008.

* cited by examiner

*Primary Examiner* — David A Vanore
*Assistant Examiner* — Nicole Ippolito
(74) *Attorney, Agent, or Firm* — Flynn, Thiel, Boutell & Tanis, P.C.

(57) ABSTRACT

Even in a case where a spark is generated in an electron beam irradiation device 28, all the vessels 2 being conveyed are sterilized by the irradiation with the electron beam. The electron beam is emitted by heating filaments 42 arranged in a vacuum chamber 40 and the vessels 2 are irradiated with the electron beam taken out into the atmosphere through a window foil 48 of an irradiation window 46 formed to an irradiation section 44. The vessels 2 are conveyed in a state of being held by vessel holding portions 36A and 36B of a vessel conveying device 24 and pass in front of the irradiation window 46. Although the electron beam irradiation is temporarily interrupted when a spark is generated, a length of the irradiation window 46 in a vessel conveying direction X is made larger than a vessel conveying distance in an interruption time.

4 Claims, 4 Drawing Sheets

ELECTRON BEAM STERILIZER

TECHNICAL FIELD

The present invention relates to an electron beam sterilizer particularly capable of surely sterilizing an object to be subjected to irradiation with the electron beam even in a case where a spark is generated in a vacuum chamber during irradiation with the electron beam.

BACKGROUND ART

An electron beam sterilizer is provided with a sterilization chamber formed of lead for preventing an electron beam or an X-ray from leaking, conveying means for conveying an object to be subjected to irradiation or processing (which may be called merely "object" or "irradiation object" hereinlater) disposed in the sterilization chamber, and an electron beam irradiator for irradiating the object in the sterilization chamber with the electron beam.

The electron beam irradiator generates thermal electron by heating a filament in a vacuum in a vacuum chamber, accelerates the electron beam by applying a high voltage to thereby create a high speed electron beam, makes the electron beam generate into the atmosphere through a metallic window foil, such as Ti (Titanium), attached to an irradiation window, and then irradiates the object to be processed with the electron beam, thus performing sterilization and the like processing.

In the electron beam sterilizer, there may be a case in which a spark is generated in the vacuum chamber in which the filaments for generating the electron beam are disposed. When the spark is generated, since the irradiation of the electron beam is not caused till a condition inside the vacuum chamber returns to the condition before the generation of the spark, any sterilizing effect is not expected, and the object may be transferred downstream side without being sterilized. Because of this reason, when the spark is generated, it is necessary to return the condition as soon as possible after stopping the operation of the irradiator. There is provided a control system for an electron beam irradiator capable of possibly shortening a time for restarting the operation of the irradiator (for example, refer to Patent Publication 1.)

The invention of the Patent Publication 1 has a structure such that when the spark is generated inside the vacuum chamber, an output of a power source of the filament is fixed to a value at that time and an output of a high voltage power source of direct current for acceleration voltage is throttled to a value corresponding to the generated spark. When the spark is extinguished, the output value of the high voltage power source of direct current is returned to a value before the generation of the spark, so that the fixing of the output of the power source of the filament is released.

Patent Publication 1: Japanese Patent Publication No. 2848136

DISCLOSURE OF THE INVENTION

Problem to be Solved by the Invention

According to the structure of the invention disclosed in the Patent Publication 1, several milliseconds or several tens of milliseconds are required for restarting the operation of a device after the stopping of the operation thereof by the generation of the spark. As mentioned, in this structure, an interruption time during the generation of the spark is controlled to be shortened. However, even in a short time, if an article passes in front of an irradiation window of the electron beam irradiator during the interruption without being irradiated with the electron beam, there is a fear that the article may be transferred downstream without being sterilized by the electron beam irradiation, thus providing inconvenient matter.

It is an object of the present invention to provide an electron beam sterilizer capable of irradiating all vessels being conveyed with an electron beam, even in a case when a spark is generated in a vacuum chamber of an electron beam irradiator and irradiation with the electron beam is interrupted.

Means for Solving the Problem

The present invention provides an electron beam sterilizer provided with electron beam irradiating means that emits an electron beam through an irradiation window and vessel conveying means that conveys a vessel passing in front of the irradiation window, in which the vessel is sterilized by being irradiated with the electron beam emitted from the electron beam irradiating means, the electron beam sterilizer being characterized in that the irradiation window has a length in the vessel conveying direction larger than a vessel moving distance during an electron beam irradiation interruption time caused by the generation of a spark by the electron beam irradiating means.

The invention is also characterized in that a plurality of irradiation windows are arranged along the vessel conveying direction and the sum of lengths of the plural irradiation windows is made larger than the vessel moving distance during the electron beam irradiation interruption time caused by the generation of the spark.

The invention is also characterized in that the vessel conveying means is provided with vessel holding means vertically holding two vessels and inverting means inverting the vertically arranged vessel holding means, the conveying means passes in front of the irradiation windows with the vessels being vertically held, and the irradiation windows are arranged vertically so that the vertically positioned vessels are irradiated with the electron beam, respectively.

Effects of the Invention

According to the electron beam sterilizer of the present invention, since an irradiation window of an electron beam irradiating means has a length, in the vessel conveying direction, to be longer than the vessel moving distance within the interruption time of the irradiation with the electron beam by the generation of the spark, even if the spark is generated, all the vessels can be surely subjected to the irradiation with the electron beam.

REFERENCE NUMERALS

2 vessel
24 vessel conveying means (vessel conveying device)

28 electron beam irradiating means (electron beam irradiator)
36A vessel holding portion (vessel holding means)
36B vessel holding portion (vessel holding means)
42 filament
46 irradiation window

BEST MODE FOR EMBODYING THE INVENTION

An electron beam sterilizer according to the present invention is provided with electron beam irradiating means for irradiating a vessel with an electron beam through an irradiation window, and vessel conveying means for conveying the vessel in front of the irradiation window of the electron beam irradiating means with the vessel being held, and has a structure such that the irradiation window has a length, in a vessel conveying direction, which is set to be longer than a distance for movement of the vessel within an irradiation interruption time by generation of the spark. Accordingly, even if the spark is generated, such an object as that all the vessels are surely subjected to the irradiation with the electron beam can be achieved

Embodiment 1

Hereunder, the present invention will be described with reference to an embodiment shown in the accompanying drawings.

Figure 2:
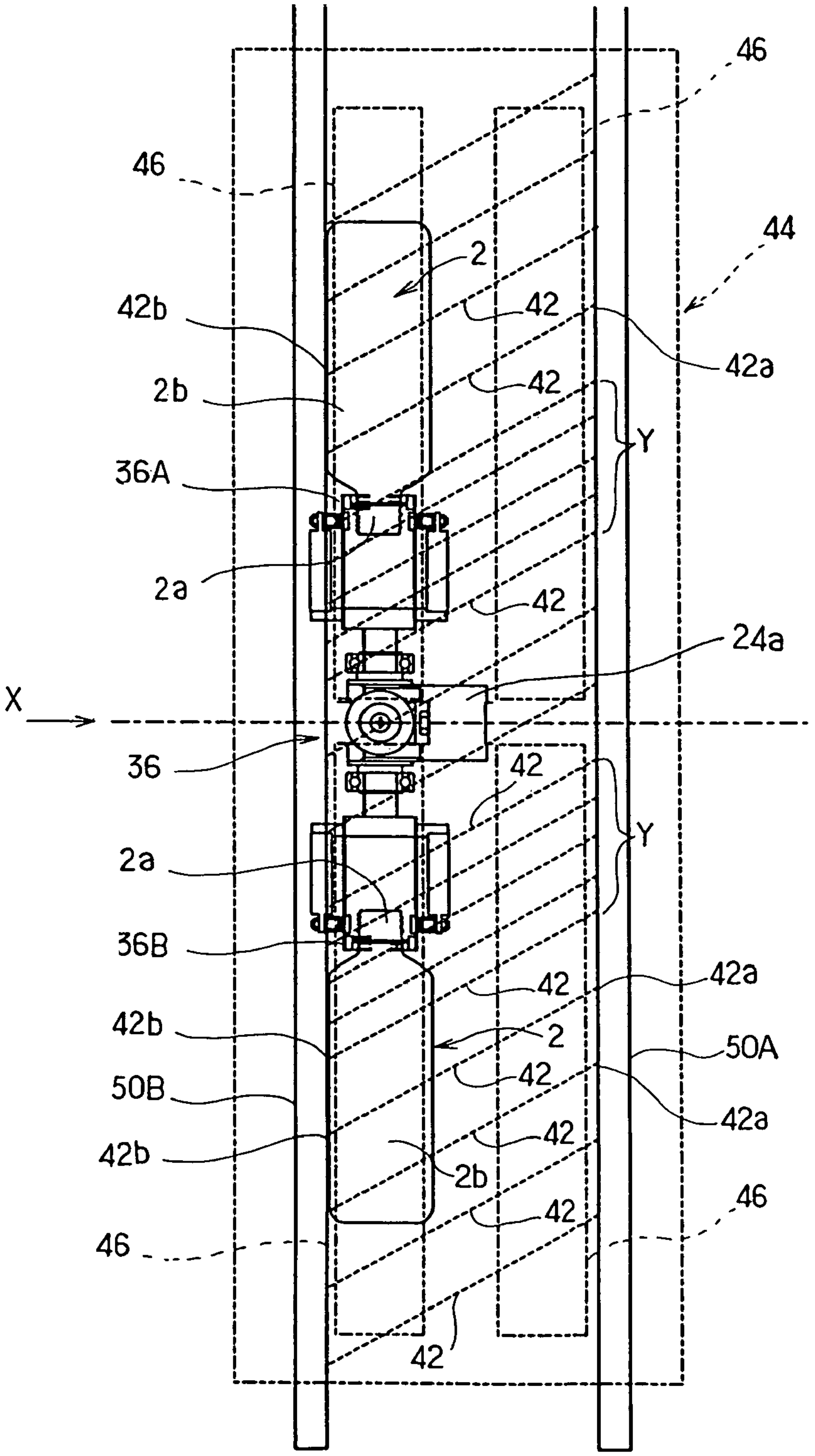
FIG. 2 is a view showing an arrangement of filaments disposed in a vacuum chamber of an electron beam irradiator, which is viewed from an arrow II in FIG. 1.
Figure 3:
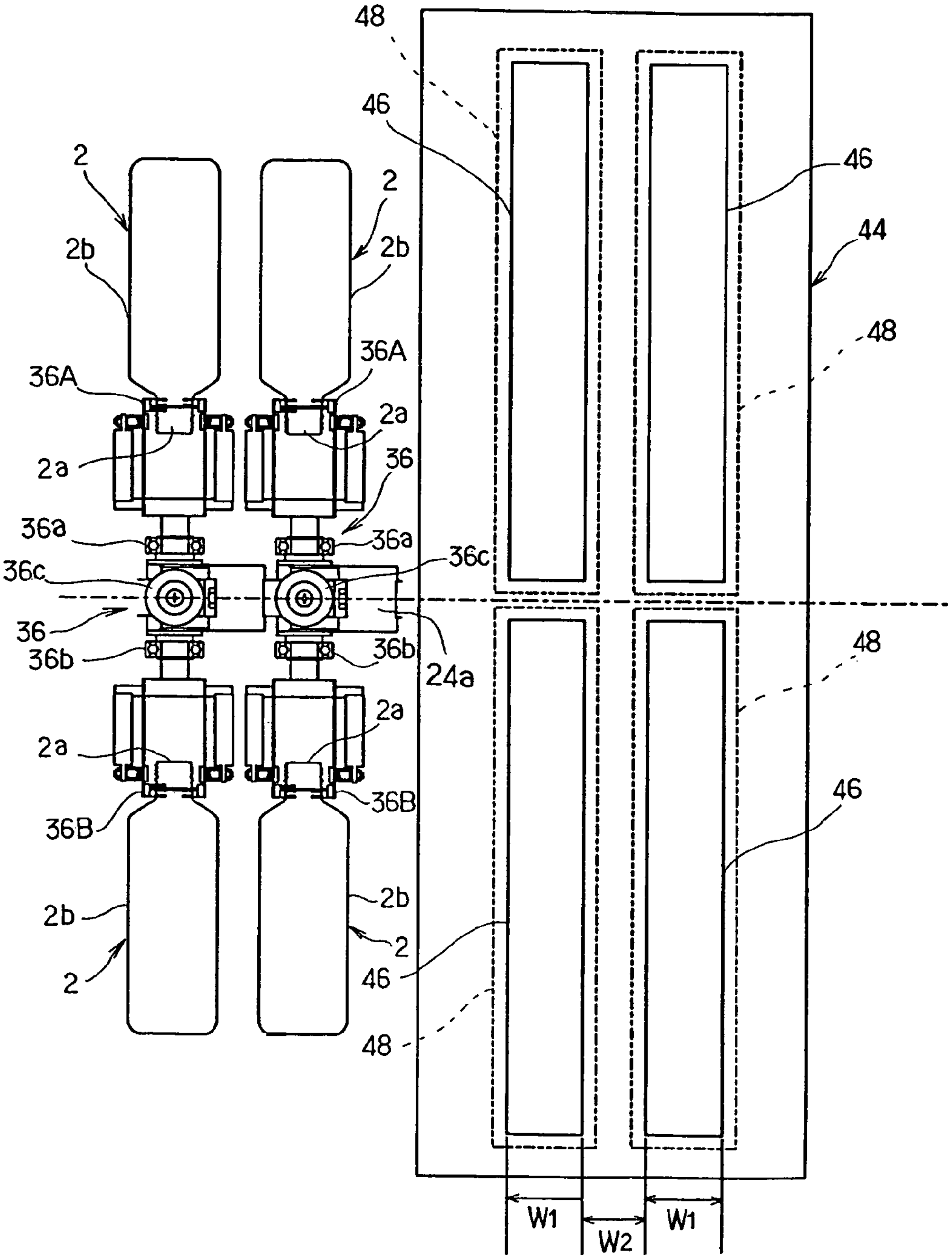
FIG. 3 is a view showing a structure of an irradiation section of the electron beam irradiator and a structure of vessel conveying means for conveying the vessels, which is viewed from an arrow III in FIG. 1.

A vessel 2, which is sterilized by the electron beam sterilizer according to the present embodiment and filled with an inner content such as liquid in a subsequent process, is a vessel made of resin such as PET bottle (refer to FIGS. 2 and 3). The vessels 2 are continuously conveyed by an air conveyer 4 and separated into each vessel with a predetermined interval by an infeed screw 6 and conveyed into an introduction chamber.

The introduction chamber is divided into two sections (a first introduction chamber 8 and a second introduction chamber 10), and two rotary wheels (a first rotary wheel 12 and a second rotary wheel 14) provided with vessel holding means, not shown, are disposed in these chambers 8 and 10, respectively. The vessels 2 introduced into these chambers 8 and 10 are subsequently transferred to the rotary wheels 12 and 14 in the respective chambers 8 and 10 and then turned and conveyed.

An opening, not shown, through which the vessel 2 can pass, is formed in a wall surface of the chamber 8 through which the vessel 2 is conveyed into the first introduction chamber 8 from the air conveyer 4. Further, another opening, not shown, through which the vessel can be transferred, is formed in a partition wall formed to a portion transferring the vessel 2 from the first rotary wheel 12 to the second rotary wheel 14.

On a downstream side of the second introduction chamber 10, is disposed a sterilization box (sterilization chamber) 18, which is defined by wall surfaces made of lead for shielding electron beams or X-rays (brake X-ray) from leaking outward at the time of irradiating the vessel 2 with the electron beam for sterilization thereof. An internal space of this sterilization box 18 is sectioned into several chambers including a supply chamber 22 on an inlet side in which a supply wheel 20 is arranged, a main chamber 26 in which the vessel 2 received from the supply wheel 20 is conveyed, and a vessel conveying device 24 for inverting upside-down in an inverting area A is disposed, an irradiation chamber 30 which is disposed in front of an electron beam irradiating device (electron beam irradiator) 28 so that the conveyed vessel 2 is irradiated with the electron beam, and a discharge chamber 32 which is continuously disposed on an outlet side (right side in FIG. 1) of the irradiation chamber 30 and in which the vessel 2 sterilized by the electron beam irradiation is fed downstream side with an aseptic condition being maintained.

An opening, not shown, through which the vessel 2 can pass, is formed to a wall surface portion of the sterilization camber 18 through which the vessel 2 is transferred to the supply wheel 20 in the supply chamber 22 from the rotary wheel 14 in the second introduction chamber 10. The supply wheel 20 receiving the vessel 2 from the second rotary wheel 14 transfers the vessel 2 to the vessel conveying device 24 disposed in the main chamber 26. An opening, not shown, through which the vessel 2 can be transferred, is also formed to a partition wall 34 between the supply chamber 22 and the main chamber 26.

The vessel conveying device 24 disposed in the main chamber 26 is provided with a vessel holding belt 24*a* and two sprockets (first sprocket 24*b* and second sprocket 24*c*). The vessel holding belt 24*a* is constructed as an endless type vessel conveying member to which a number of vessel gripper 36 as vessel holding means (refer to FIGS. 2 and 3 described latter), and the two sprockets are constructed as transfer rotary body for circularly conveying the vessel grippers 36 around which the endless vessel holding belt 24*a* is wound.

Each of the vessel grippers 36 has a vertical pair of vessel holding portions 36A and 36B (recited as vessel holding means in claim 3), which serve to simultaneously convey two vessels 2 in a holding state, and the respective grippers 36 are rotatable around the axial line along the conveying direction, thus the vessel grippers 36 being vertically inverted by rotating by 180 degrees during the conveying movement. Each of the vessel holding portions 36A and 36B of each vessel gripper 36 holds a neck portion of the vessel (PET bottle) (in this embodiment, a portion, just above an inclining shoulder portion of the vessel 2, to be held by the gripper 36 is called "neck portion", and an upper entire thickened portion including this neck portion is called "mouth portion" 2*a*), and the vessels 2 held by the vessel holding portions 36A and 36B are conveyed in a state in which the mouth portions 2*a* of the vessels 2 are opposed to each other.

The vessel conveying device 24 is composed of a linear path line along which the vessel gripper 36 is linearly moved between both the sprockets 24*b* and 24*c*, and a circular path line along the respective sprockets 24*b* and 24*c*. The inverting area A mentioned hereinbefore is provided for the linear path line extending from the second sprocket 24*c* to the first sprocket 24*b*, and during the conveyance of the vessel 2 around one circle, the vessel 2 is inverted (turned over) vertically.

Figure 4:
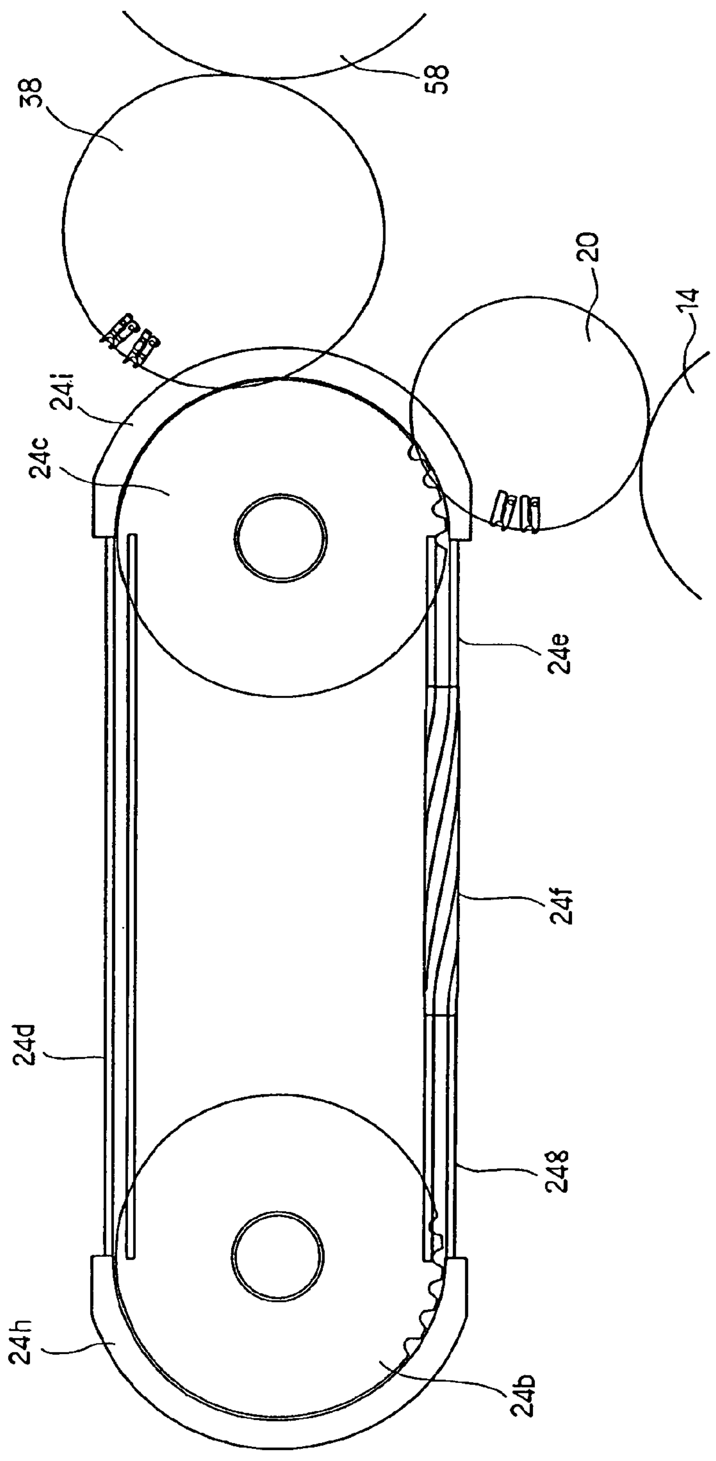
FIG. 4 is a plan view showing a circulation movement path constituting the vessel conveying means.

FIG. 4 is a view, in an enlarged scale, showing a circularly moving path including two sprockets 24*b* and 24*c* around which the endless vessel holding belt 24*a* (refer to FIG. 1), partially shown in FIGS. 2 and 3, and a linear guide and an inverting guide which guide the vessel holding belt 24*a* traveling between these two sprockets 24*b* and 24*c*. With reference to FIG. 4, a structure for turning around the gripper 36 will be simply explained.

A linear guide 24*d* composed of upper and lower, and right and left, four total, parallel rails are arranged on the conveying path extending from the first sprocket 24*b* to the second sprocket 24*c* and, as shown in FIG. 3, a vertical pair of rollers 36*a* and 36B and a pair of side rollers 36*c* (only one of which is shown) arranged at right and left portions in the advancing direction are provided in a state held between four rails of the linear guide 24*d*, and these rollers travel with both the grippers 36 being maintained on the vertically linear line. The irradiation chamber 30 is disposed at an area in which the grippers are conveyed under the guidance of the linear guide 24*d*, and the vessel 2 held by the gripper 36 is irradiated with the electron beam during the passing within the irradiation chamber 30.

Further, an upstream side linear guide 24*e*, an intermediate inverting guide 24*f* and a downstream side linear guide 24*g* are constructed, by continuous four rails, on the conveying path extending from the second sprocket 24*c* to the first sprocket 24*b*.

The upstream side and downstream side linear guides 24*e* and 24*g* are composed of four rails in vertically and laterally parallel to each other, like the linear guide 24*d* mentioned hereinbefore, and a pair of vessel holding portions 36A and 36B of the gripper 36 are conveyed with the vertically linear state being maintained.

The intermediate inverting guide 24*f* serves, with the parallel state of the four rails being maintained, such that upper two rails of the upstream side linear guide 24*e* move toward a lower side and lower two rails thereof move to an upper side, and the upper and lower rollers and the side rollers 36*c* of the gripper 36 held by the respective rails are changed in their positions by 180 degrees, thereby vertically inverting the vertical positions of the two vessel holding portions 36A and 36B. This inverting guide 24*f* is arranged in the inverting area A shown in FIG. 1 and constitutes inverting means. Further, circular guides 24*h* and 24*i* are disposed on outer peripheral sides of the first sprocket 24*b* and the second sprocket 24*c* to thereby guide the traveling of the vessel holding belt 24*a*.

The upstream side and downstream side linear guides 24*e* and 24*g* are composed of four rails in vertically and laterally parallel to each other as like as the linear guide 24*d* mentioned hereinbefore, and a pair of vessel holding portions 36A and 36B of the gripper 36 are conveyed with the vertically linear state being maintained.

The intermediate inverting guide 24*f* serves, with the parallel state of the four rails being maintained, such that upper two rails of the upstream side linear guide 24*e* move toward a lower side and lower two rails thereof move to an upper side, and the upper and lower rollers and the side rollers 36*c* of the gripper 36 held by the respective rails are changed in their positions by 180 degrees, thereby vertically inverting the vertical positions of the two vessel holding portions 36A and 36B. This inverting guide 24*f* is arranged in the inverting area A shown in FIG. 1 and constitutes inverting means recited in claim 3. Further, circular guides 24*h* and 24*i* are disposed on outer peripheral sides of the first sprocket 24*b* and the second sprocket 24*c* to thereby guide the traveling of the vessel holding belt 24*a*.

A vessel supply position B is set on the downstream side of the conveying direction of the vessel gripper 36 in the circular path of the second sprocket 24*c*, and a vessel discharge position C is also set on the upstream side thereof (refer to FIG. 1) in a manner such that one vessel 2 is held by one of the vessel holding portions 36A and 36B at the vessel supply position B and then conveyed by two turns, and during this conveyance, the vertical position is inverted twice to return to the position of the vessel supply time, and thereafter, the vessel 2 is transferred to the receiving wheel 38 of the discharge chamber 32 from the vessel discharge position C. The interiors of the first introduction chamber 8, the second introduction chamber 10, the supply chamber in the sterilization box 18 and the main chamber 26 are controlled and managed so as to keep a positive pressure in comparison with the exteriors thereof, but are not maintained in completely aseptic condition, because the vessel 2 before the sterilization is introduced therein and conveyed from the outside.

The electron beam irradiation means (electron beam irradiation device) 28 is arranged adjacent to the sterilization box 18 made of lead. The electron beam irradiation device 28 is provided with a vacuum chamber (acceleration chamber) 40 for irradiating the vessel 2 with the electron beam and is rested on a mount table 41 to be movable along rails 41*a*. The electron beam irradiation device 28 serves, as is well known, to heat the filaments 42 (refer to FIG. 2) in the vacuum in the vacuum chamber 40 and generate the electron beam, then accelerate the electron beam by applying high voltage to create high speed electron beam, and take out into atmosphere throughout a window foil 48 (refer to FIGS. 2 and 3) of metal material such as Ti formed to an irradiation section 44 to thereby perform processing such as sterilization processing by irradiating an object to be processed (vessel 2 in this embodiment) with the electron beam.

The electron beam irradiation device 28 of this embodiment is provided, as shown in FIGS. 2 and 3, with four irradiation windows 46 to the irradiation section 44. The vessel gripper 36 of this embodiment serves to hold and convey simultaneously two vessels 2 by the vertically arranged two vessel holding portions 36A and 36B, and accordingly, the two vessels 2 are irradiated with the electron beams so that the irradiation windows 46 are independently in the vertical positions so as to correspond to the vertical two vessels 2, respectively.

Furthermore, in the electron beam irradiation device 28, there may be a case in which a spark is generated within the vacuum chamber (acceleration chamber) 40 in which the filaments 42 for generating the electron beam is arranged, and when such spark is generated, the electron beam irradiation is interrupted. This interruption is recovered in a short time, but if the vessel 2 is passing in front of the irradiation window 46 during this interruption, this vessel 2 is not irradiated with the electron beam and is hence not sterilized thereby. Therefore, even if the electron beam irradiation is interrupted by the generation of the spark, a sufficient length is ensured in the vessel conveying direction (shown with symbol X in FIGS. 2 and 3) so that all the vessels are surely irradiated with the electron beam, even in the interruption of the electron beam irradiation by the generation of the spark. For this purpose, it may be possible to provide a single irradiation window having a sufficiently long length in the vessel conveying direction. However, since there is a limit to the size of the metal window foil mounted to the irradiation window, in this embodiment, two irradiation windows 46 are arranged side by side in the vessel conveying direction to ensure the necessary length.

Hereunder, a specific example for the length in the vessel conveying direction X of the irradiation window 46 will be explained.

A time required for the recovery of the condition before the spark generation from the generation of the spark in a case when the spark is generated in the vacuum chamber 40 is less than 0.1 second (several milliseconds to several tens milliseconds) and, accordingly, it may be necessary to set the maximum interruption time to be 0.1 second. For example, in assuming processing ability (capacity) of the sterilization device (sterilizer) according this embodiment being 600 bpm and the vessel conveying speed being 56 m/min., the vessel 2 held by the vessel gripper 36 and conveyed in this state is moved by 93 mm by 0.1 second. Accordingly, the length of the irradiation window 46 in the vessel conveying direction is set to be more than 93 mm. That is, supposing that a spark is generated at a time when the vessel 2 reaches the upstream side end of the irradiation window 46 and the electron beam irradiation is interrupted by 0.1 second, the vessel 2 advances by 93 mm during this interruption, and therefore, in a case where the length of the irradiation window 46 in the vessel conveying direction X is shorter than 93 mm, the vessel 2 had already been passed in front of the irradiation window 46 or partially passed at the time of the recovery of the electron beam irradiation, so that there causes a case that the electron beam irradiation is not performed or insufficiently performed.

On the other hand, as mentioned above, by taking the arrangement in which the length of the irradiation window 46 in the vessel conveying direction X is made longer than 93 mm, the vessel 2 can be irradiated with the electron beam in the entire area in the vessel conveying direction. In the embodiment shown in FIG. 3, one of the irradiation windows 46 has a width W1 (length in the vessel conveying direction X) has 65 mm, and an interval W2 between two irradiation windows 46 is set to be 55 mm, and accordingly, in this embodiment, although the moving distance of the vessel 2 by 0.1 second is 93 mm, the irradiation windows have a length of 130 mm (i.e., 65 mm×2). Further, in this embodiment, although necessary length can be ensured by arranging the two windows 46 side by side in the vessel conveying direction X, the number of the irradiation windows is not limited "two" and three or more than three irradiation windows 46 may be provided side by side in the vessel conveying direction X in accordance with the vessel conveying speed or other conditions.

As for the filament 42 of the electron beam irradiation device 28, a plurality of filaments may be arranged in parallel with each other as shown in FIG. 2 and in an inclined manner with respect to the vessel conveying direction X. It is necessary for the filaments 42 to be arranged in a manner that one filament 42 and another one filament 42 adjacent to this one filament 42 are overlapped each other. That is, one ends (right ends 42*a* in the illustration of FIG. 2) and other one ends (left ends 42*b*) positioned above the one ends 42*a* are necessarily overlapped each other on the vessel conveying direction X, respectively. That is, the entire portions of the vessels 2 conveyed across the front portion of the irradiation windows 46 pass in front of the filaments 42, so that all the surfaces of the vessel 2 is irradiated with the electron beam with the necessary amount.

The electron beam irradiation device 28 according to this embodiment is an area irradiation-type (non-scan type), and the filaments 42 are arranged so as to cover all the area of the four irradiation windows 46. Both the ends 42*a* and 42*b* of all the filaments 42 are connected to electric power supply members 50A and 50B so as to be applied with electric power.

Furthermore, in the electron beam irradiation device 28 of this embodiment, the filaments 42 are arranged densely to be concentrated at portions through which the mouth portions 2*a* of the vessels 2 (shown with symbol "Y" in FIG. 2) pass in comparison with portions through which the other portions of the vessels 2 such as shell portions 2*b* of the vessels 2 pass. Accordingly, the mouth portion 2*a* of the vessel 2 passing in front of the densely arranged filaments 42 receives a large amount of electron beam in comparison with the shell portion 2*b* of the vessel. In other words, by increasing the distance between the adjacent filaments 42 in front of which the shell portion 2*b* of the vessel 2 passes more than that in a conventional structure, the amount of the electron beam to be irradiated to the shell portion 2*b* of the vessel 2 can be made less than that in the conventional structure.

In this embodiment, the mount table 41 on which the electron beam irradiation device 28 rests is constructed to be movable on the rails 41*a* so as to approach or separate from the sterilization box 18. When the electron beam sterilizer is operated, the mount table 41 is moved close to the sterilization box 18, the irradiation section 44 of the vacuum chamber 40 accords with the opening 18*a* formed to the wall surface of the sterilization box 18, and the sterilization box 18 and the electron beam irradiation device 28 are coupled. The irradiation chamber 30 is provided inside the sterilization box 18 so as to surround the opening 18*a* to which the irradiation section 44 of the vacuum chamber 40 is coupled. In the vessel conveying device 24, the linear path line extending from the sprocket 24*b* to the sprocket 24*c* penetrates the irradiation chamber 30, and the irradiation portion (irradiating section) D is set to this penetrating portion. The two vessels 2 held by both the vessel holding portions 36A and 36B of the vessel gripper 36 pass inside the irradiation chamber 30 in the vertically perpendicular attitude, and the respective vessels 2 are subjected to the irradiation with the electron beam from the electron beam irradiation device 28 at this irradiation portion D.

Openings, not shown, are formed in the wall surfaces on the inlet side and the outlet side of the irradiation chamber 30 so that the vertically arranged two vessels 2 held by the vessel gripper 36 pass through the openings. The discharge chamber 32 is provided to be continuous to the wall surface on the outlet side of the irradiation chamber 30. One of the sprockets (right side sprocket 24*c* in FIG. 1) of the vessel conveying device 24 is intruded into the discharge chamber 32, and the vessel 2 held by the vessel gripper 36 and irradiated with the electron beam at the respective vertical positions (totally twice) is transferred to the receiving wheel 38 set in the discharge chamber 32 from the vessel holding portion 36A or 36B positioned on the lower side of the vessel gripper 36. The discharge chamber 32 is surrounded by: a partition wall 54 dividing, without blocking the rotation of the sprocket 24*c*, the conveying path of the vessel conveying device 24 from the opening on the outlet side of the irradiation chamber 30 to the transferring wheel 38 and the conveying path of the transfer wheel 38 from the main chamber 26 and the supply chamber 22; a partition wall 54 opposing to the partition wall 52 and dividing from the upper and lower space of the transfer wheel 38; a floor surface of the sterilization box 18; and a ceiling surface of the sterilization box 18. The respective chambers disposed on the downstream side from this discharge chamber 32 are maintained in an aseptic condition for processing the vessel 2 sterilized by the electron beam irradiation.

Figure 1:
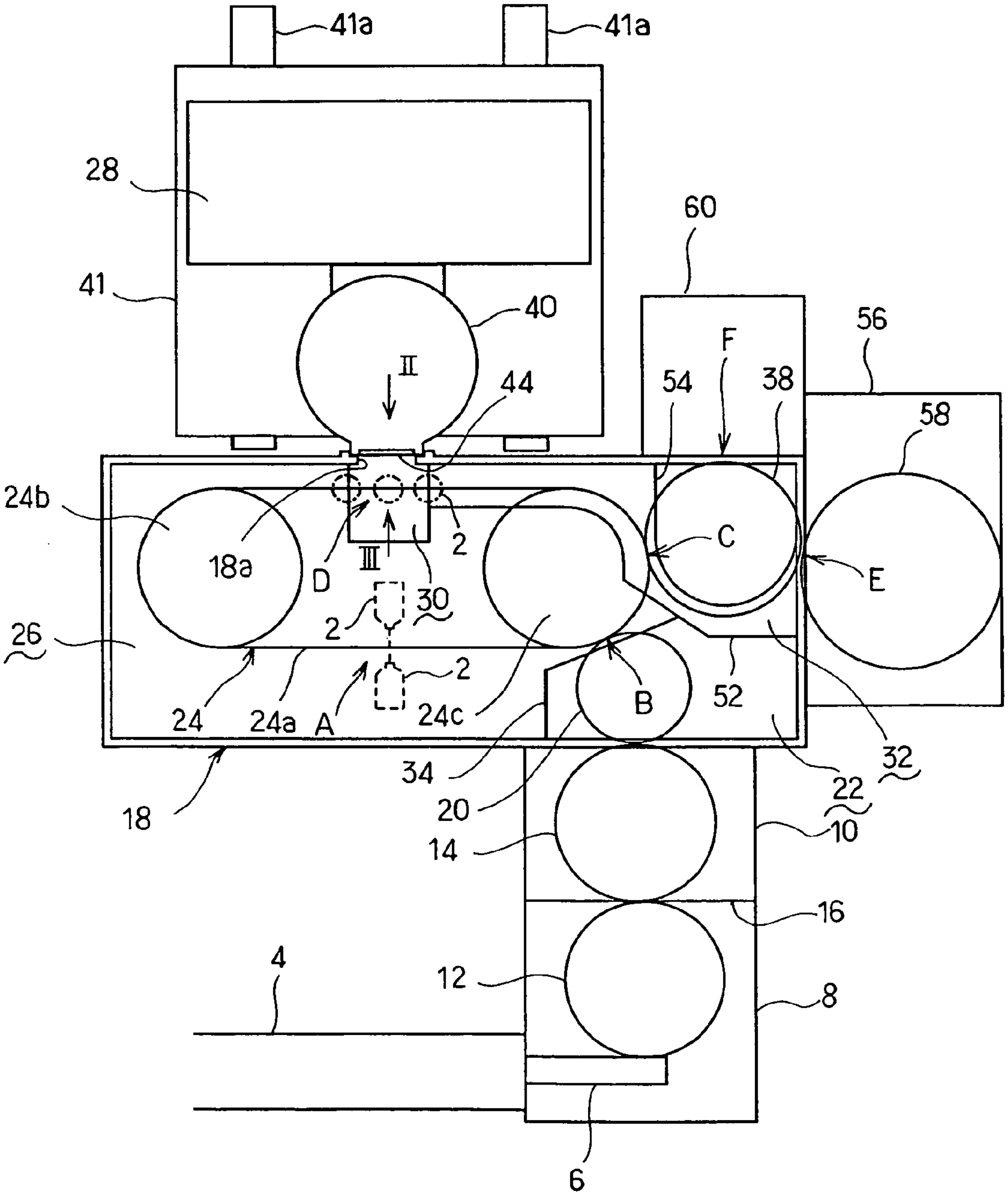
FIG. 1 is a plan view illustrating an entire structure of an electron beam sterilizer (embodiment 1).

An intermediate chamber 56 is disposed adjacent to the discharge chamber 32 positioned on the most downstream side within the sterilization box 18, and a chamber, not shown, in which a filler and so on are housed is disposed further downstream side of the intermediate chamber 56. A rotary wheel (neck wheel) 58 provided with vessel holding means, not shown, is disposed within the intermediate chamber 56, and this neck wheel 58 receives the vessel 2 from the transfer wheel 38 in the discharge chamber 32. The neck wheel 58, after receiving the vessel 2, turns and transfers the vessel 2 to a supply wheel disposed in the chamber in which the filler is arranged. A position shown with the letter "E" in FIG. 1 is the transfer position at which the vessel 2 is transferred from the transfer wheel 38 of the discharge chamber 32 to the neck wheel 58 of the intermediate chamber 56.

The transfer wheel 38 disposed in the discharge chamber 32 also serves as an intermediate reject wheel, so that in a case when it is judged that the vessels 2 can be always properly sterilized by information form respective sensors, the vessels 2 received from the vessel conveying device 24 are transferred to the neck wheel 58 of the intermediate chamber 56 so as to be subjected to the next processing, but in a case when it is judged that the vessel 2 is not irradiated with the electron beam or that the sterilization is insufficiently performed, the vessel 2 is not transferred to the neck wheel 58 of the intermediate chamber 56 and is discharged into a reject chamber 60 disposed in adjacent to the sterilization box 18. The letter "F" in FIG. 1 shows a vessel reject position.

The generation of the spark is detected in the electron beam irradiation device 28, and when the spark is generated, a detection signal is outputted to a controller, not shown. The controller recognizes a pulse of an encoder of the vessel conveying device 24 at the timing of inputting the signal and specifies the vessel 2 in question, and the fact that this vessel 2 reaches the reject position "F" is detected by counting the pulses and rejects this vessel 2. In this case, all the vessels 2 positioned in front of the irradiation window 46 at the irradiation of the electron beam caused by the generation of the spark are rejected.

An operation of the electron beam sterilizer of the structure mentioned above will be described hereunder.

The vessels 2 which are sterilized by this sterilizer and filled with inner liquid are PET bottles, which are conveyed by blowing air from the rear side thereof by a propelling blower in a state in which lower sides of flange portions formed to the neck portions of the PET bottles are held by support rails, not shown, of the air conveyer 4. The vessels 2 conveyed by the air conveyer 4 are introduced into the first introduction chamber 8, in which the vessels 2 are separated by a predetermined interval by the infeed screw 6 and then transferred to the vessel holding means of the first rotary wheel 12. The vessels 2 are transferred to the second rotary wheel 14 within the second introduction chamber 10 after being rotated and conveyed by the first rotary wheel 12.

The vessel 2 is transferred to the supply wheel 20 disposed in the supply chamber 22 of the sterilization box 18 made of lead from the second rotary wheel 14, held by the vessel holding means of the supply wheel 20, rotated and conveyed in this state, and then transferred to the vessel gripper 36 of the vessel conveying device 24. The vessel gripper 36 is provided with two vessel holding portions 36A and 36B vertically arranged, and the vessel 2 held by the lower side vessel holding portion 36A or 36B is moved upward by the inversion of the vessel gripper 36 in its vertical position in the inverting area A to thereby take an inverted attitude. The inverted vessel 2 is moved so as to turn around the first sprocket 24*b* and then enters the irradiation chamber 30. The interior of the irradiation chamber 30 is irradiated with the electron beam emitted from the electron beam irradiation device 28 disposed outside the irradiation chamber 30, and the vessel 2 now being conveyed passes in front (irradiation position D) of the irradiation window 46 formed to the irradiating portion 44 of the vacuum chamber 40.

Thermal electrons generated in the vacuum chamber 40 by heating the filaments 42 are accelerated by applying high voltage to create high velocity electron beam, and thereafter, the interior of the irradiation chamber 30 is irradiated with the electron beam through the window foil 48 such as Ti attached to the irradiation window 46, thus irradiating, with the electron beam, the vessel 2 conveyed within the irradiation chamber 30 in the state held by the vessel holding portion 36A or 36B of the vessel gripper 36 and sterilizing the vessel 2.

In this embodiment, as shown in FIG. 2, the filaments 42 disposed to the portion in front of which the mouth portions 2*a* above the neck portions held by the vessel holding portions 36A and 36B pass are densely arranged (refer to the filaments disposed in the area shown with "Y" in FIG. 2) in comparison with the filaments 42 disposed to the other portion. Therefore, the irradiation amount of the electron beam irradiating the mouth portion 2*a* of the vessel 2 is increased in comparison with an arrangement of a conventional structure, and accordingly, the thickened mouth portion 2*a* can be surely sterilized.

Recently, the shell portion of the PET bottle has been made thin for the purpose of making its weight light, and on the other hand, it is necessary for the mouth portion 2*a* to be thickened more than the shell portion 2*b* because the mouth portion 2*a* is mounted with a cap to tightly seal the vessel 2. Accordingly, if the shell portion 2*b* and the mouth portion 2*a* of the vessel 2 are irradiated with the electron beam of the same irradiation amount, there is a fear that the shell portion 2*b* is excessively irradiated with the electron beam, and hence, may be deformed, or that the mouth portion 2*a* is less irradiated, and hence, may be insufficiently sterilized. In this embodiment, however, as mentioned above, the arrangement of the number of the filaments 42 is made different in the positions where the shell portion 2*b* and the mouth portion 2*a* pass, respectively, so that the mouth portion 2*a* of the PET bottle 2 can be surely sterilized as well as the shell portion 2*b* thereof can be prevented from being deformed by preventing the excessive electron beam irradiation to the shell portion 2*b*.

The vessel 2 passing through the irradiation chamber 30 after the first irradiation therein as mentioned above enters the discharge chamber 32, rotates and moves around the sprocket 24*c* and then again returns to the supply position B at which the vessel 2 is supplied from the supply wheel 20. The vessel 2 received by the lower side vessel holding portion 36A or 36B from the supply wheel 20 in the previous operation has been inverted and moved upward, and the other vessel holding portion 36B or 36A positioned on the lower side at that time receives the vessel 2 from the supply wheel 20. Thereafter, the vessel gripper 36 is again inverted in the inverting area A to change the vertical position thereof, and the vessel 2 which was subjected to the electron beam irradiation in the previous operation (first time irradiation) at the upper position is moved to the lower position, so that the surface of the vessel 2 which was not subjected to the electron beam irradiation faces outward in the rotating and moving direction of the vessel conveying device 24. When the vessel gripper 36 holding two vessels 2 again enters the irradiation chamber 30, the vessel 2 which had already been subjected to the first time irradiation is subjected to second time electron beam irradiation from the side opposite to the side irradiated in the previous first time irradiation, thus irradiating the entire inner and outer surfaces of the vessel 2, which is hence sterilized, and in the same time, the vessel 2 newly held and positioned on the upper side is subjected to the first time irradiation.

According to this embodiment, the vessel gripper 36 is provided with two vessel holding portions 36A and 36B arranged vertically so that two vessels 2 are simultaneously held and conveyed, and irradiated with the electron beam in the irradiation chamber 30. In addition, as to the arrangement of the filaments 42, since the filaments 42 are densely arranged as shown with "Y" to the portions at which the mouth portions 2*a* of the vessels 2 pass, only the mouth portions 2*a* are sufficiently subjected to the second time electron beam irradiation as in the first time irradiation to thereby perform the complete sterilization, and the shell portions 2*b* are on the other hand subjected to the electron beam irradiation in proper amounts without being excessively irradiated. The vessel 2 which had been subjected to the second time electron beam irradiation in the irradiation chamber 30 and sterilized at the entire inner and outer surfaces thereof is transferred to the transfer wheel 36 at the discharge position C in the discharge chamber 32. The vessel 2 is transferred thereafter to the neck wheel 58 disposed in the intermediate chamber 56, and then discharged from the sterilization box 18 made of lead.

The electron beam irradiation device 28 may cause an occasion of generating a spark, and in such occasion, the electron beam irradiation is temporarily interrupted. Thereafter, a time required for recovering the electron beam irradiation is maximally 0.1 second, and since there is provided the irradiation window 46 having the length larger than the distance by which the vessel 2 held by the vessel gripper 36 of the vessel conveying device 24 is moved in 0.1 second, all the vessels 2 can be subjected to the electron beam irradiation, even if the spark is generated. However, in the interruption of the electron beam irradiation by the generation of the spark, there may be a case where the electron beam irradiation is not made with sufficient irradiation amount according to the irradiating conditions, such as electron beam intensity, irradiation time, vessel conveying speed and the like, preliminarily set to the electron beam irradiation device other than the case where a sufficient amount of the electron beam for the sterilization of the vessel is obtained. In such a case, the present embodiment has the structure capable of rejecting all the vessels 2 passing in front of the irradiation window 46 during the interruption of the electron beam irradiation by the generation of the spark. As to the vessels 2 to be rejected, as mentioned hereinbefore, the controller in which the spark detection signal is inputted specifies the vessels to be rejected by recognizing the pulse of the encoder of the vessel conveying device 24 at the spark detection signal input timing, and the vessel 2 is rejected by detecting the fact that this vessel 2 reaches the rejection position "F" by counting the pulses. According to the present invention, in the case where the vessel is rejected by the generation of the spark, the vessel can be surely subjected to the electron beam irradiation either before or after the generation of the spark. Accordingly, even if the structure is made such that the vessel to be rejected is conveyed from the irradiation chamber 30 to the discharge chamber 32 in the aseptic condition, the vessel which is not subjected to the sterilization is never conveyed into the aseptic atmosphere continuous to the discharge chamber 32 maintaining the aseptic condition, thus preventing any bacteria from being brought into the aseptic atmosphere.

The invention claimed is:

1. An electron beam sterilizer provided with electron beam irradiating means (28) that irradiates electron beam through an irradiation window (46) and vessel conveying means (24) that conveys a vessel (2) passing in front of the irradiation window (46), in which the vessel (2) is sterilized by irradiating the vessel (2) with the electron beam emitted from the electron beam irradiating means (28), characterized in that the irradiation window (46) has a length in the vessel conveying direction (X) larger than a vessel moving distance during an electron beam irradiation interruption time caused by generation of a spark by the electron beam irradiating means (28), the electron beam irradiation means (28) is arranged to output a detection signal when the spark is generated and the detection signal is input from the electron beam irradiation means to a controller, the controller recognizes a pulse of an encoder of the vessel conveying means (24) and specifies the vessel in question which passes in front of the irradiation window while the electron beam irradiation is interrupted so as to reject the vessel at a given reject position and the irradiation window has a length in the vessel conveying direction (X) larger than a vessel moving distance during an electron beam irradiation interruption time caused by generation of a spark by the electron beam irradiating means (28) so as to allow the rejected vessel to be subject to the electron beam irradiation.

2. The electron beam sterilizer according to claim 1, wherein a plurality of the irradiation windows (46) are arranged along the vessel conveying direction, and the sum of lengths of the plural irradiation windows (46) is made larger than the vessel moving distance during the electron beam irradiation interruption time caused by the generation of the spark.

3. The electron beam sterilizer according to claim 1, wherein the electron beam irradiation means (28) temporarily interrupts the electron beam irradiation when the generation of the spark is detected during the irradiating with the electron beam.

4. The electron beam sterilizer according to claim 2, wherein the electron beam irradiation means (28) temporarily interrupts the electron beam irradiation when the generation of the spark is detected during the irradiating with the electron beam.

* * * * *